US00PP18896P2

(12) United States Plant Patent
Hooijman

(10) Patent No.: US PP18,896 P2
(45) Date of Patent: Jun. 10, 2008

(54) ROSE PLANT NAMED 'ESM FANT'

(50) Latin Name: *Rosa hybrida*
Varietal Denomination: Esm Fant

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/700,683

(22) Filed: Jan. 30, 2007

(51) Int. Cl.
*A01H 5/00* (2006.01)

(52) U.S. Cl. ..... Plt./140

(58) Field of Classification Search ..... Plt./140
See application file for complete search history.

(56) References Cited

PUBLICATIONS

UPOVROM search for cultivar ESM FANT PBR 20050967 p. 1.*

* cited by examiner

*Primary Examiner*—Annette H Para
(74) *Attorney, Agent, or Firm*—C. A. Whealy

(57) ABSTRACT

A new and distinct cultivar of Rose plant named 'Esm Fant', characterized by its long and upright flowering stems; uniform and freely flowering habit; dark red-colored flowers; and excellent postproduction longevity.

1 Drawing Sheet

Botanical designation: *Rosa hybrida.*
Cultivar denomination: 'Esm Fant'.

BACKGROUND OF THE INVENTION

The present Invention relates to a new and distinct cultivar of Rose plant, botanically known as *Rosa hybrida,* commercially used as a cut flower Rose, and hereinafter referred to by the name 'Esm Fant'.

The new Rose is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new cultivar originated from a cross-pollination made by the Inventor in May, 2001 of a proprietary Rose selection identified as code number 90, not patented, as the female, or seed, parent with a proprietary Rose selection identified as code number 42, not patented, as the male, or pollen, parent. The cultivar Esm Fant was discovered and selected by the Inventor as a single flowering plant within the progeny of the stated cross-pollination in a controlled environment in El Quinche, Pichincha, Ecuador.

Asexual reproduction of the new Rose by cuttings at El Quinche, Pichincha, Ecuador since August, 2002, has shown that the unique features of this new Rose are stable and reproduced true to type in successive generations of asexual reproduction.

SUMMARY OF THE INVENTION

The following traits have been repeatedly observed and are determined to be the unique characteristics of 'Esm Fant'. These characteristics in combination distinguish 'Esm Fant' as a new and distinct cultivar:

1. Long and upright flowering stems.
2. Uniform and freely flowering habit.

3. Dark red-colored flowers.
4. Excellent postproduction longevity.

Plants of the new Rose differ from plants of the parent selections in the following characteristics:

1. Plants of the new Rose have longer flowering stems than plants of the parent selections.
2. Plants of the new Rose are more freely flowering than plants of the parent selections.
3. Plants of the new Rose and the parent selections differ in flower color.

Plants of the new Rose can be compared to plants of the Rose cultivar Red Mikado, not patented. In side-by-side comparisons conducted in El Quinche, Pichincha, Ecuador, plants of the new Rose differed from plants of the cultivar Red Mikado in the following characteristics:

1. Plants of the new Rose had longer flowering stems than plants of the cultivar Red Mikado.
2. Plants of the new Rose were more freely branching than plants of the cultivar Red Mikado.
3. Plants of the new Rose flowered later than plants of the cultivar Red Mikado.
4. Plants of the new Rose were more freely flowering than plants of the cultivar Red Mikado.
5. Flowers of plants of the new Rose were longer-lasting than flowers of plants of the cultivar Red Mikado.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the top of the sheet comprises a side perspective view of a typical flowering stem of 'Esm Fant'.

The photograph at the bottom of the sheet is a close-up view of a typical flower of 'Esm Fant'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown in El Quinche, Pichincha, Ecuador, in a polyethylene-covered greenhouse and under commercial production practices. Plants were about 1.5 years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* cultivar Esm Fant.

Parentage:

*Female, or seed, parent.*—Proprietary seedling selection of *Rosa hybrida* identified as code number 90, not patented.

*Male, or pollen, parent.*—Proprietary seedling selection of *Rosa hybrida* identified as code number 42, not patented.

Propagation:

*Type.*—By cuttings.

*Time to initiate roots.*—About seven to ten days at 26° C. to 30° C.

*Time to produce a rooted young plant.*—About four to five weeks at 22° C. to 26° C.

*Root description.*—Fibrous, thick.

*Rooting habit.*—Freely branching; moderately dense.

Plant description:

*Plant form.*—Upright plant habit; long and upright flowering stems.

*Growth habit.*—Moderately vigorous. Freely basal branching habit; about nine lateral branches develop from the pinching; dense and bushy growth habit; about twelve flowering stems develop per year.

*Plant height.*—About 128 cm.

*Plant width* (*spread*).—About 70 cm.

*Lateral branches.*—Length: About 115 cm. Diameter: About 7.4 mm. Internode length: About 2.5 cm. Strength: Strong. Texture: Smooth, glabrous. Color: Close to 146A. Thorns: Density: Moderate. Shape: Triangular with sharp acuminate apices. Height: About 3 mm to 5 mm. Diameter, at base: About 1 mm to 2 mm. Color, immature: close to 145C. Color, mature: Close to 166C.

Foliage description:

*Arrangement.*—Alternate; compound with five leaflets per leaf.

*Leaf length.*—About 15.8 cm.

*Leaf width.*—About 11 cm.

*Leaflet shape.*—Ovate.

*Leaflet apex.*—Cuspidate.

*Leaflet base: Attenuate.*

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Close to N77B. Developing leaflets, lower surface: Close to 166A. Fully expanded leaflets, upper surface: Close to 147A; venation, close to 200D. Fully expanded leaflets, lower surface: Close to 147B; venation, close to 144B.

*Petioles.*—Length: About 2.5 cm. Diameter: About 1 mm. Texture, upper and lower surfaces: Smooth. Color, upper and lower surfaces: N144D; wings, 146A.

Flower description:

*Flower type and habit.*—Dark red-colored flowers with numerous petals. Consistently symmetrical rosette flowers. Freely and uniformly flowering; flowers arranged in terminal corymbs with about twelve open flowers and flower buds per corymb. Flowers persistent.

*Flowering season.*—Year-round under greenhouse conditions, optimal flowering from spring through autumn under garden conditions; flowering intermittent.

*Inflorescence height.*—About 24 cm.

*Inflorescence width.*—About 21 cm.

*Flower diameter.*—About 7.2 cm.

*Flower depth* (*height*).—About 3.1 cm.

*Flower longevity on plant.*—About 36 days.

*Flower longevity as a cut flower.*—About 20 days.

*Fragrance.*—Not detected.

*Flower buds* (*at stage of showing color*).—Shape: Ovoid. Length: About 3.1 cm. Diameter: About 2.6 cm. Color: Close to 165A; towards the base, close to 143A.

*Petals.*—Quantity: Numerous; about 36 per flower. Length: About 3.9 mm. Width: About 4 cm. Shape: Broadly obovate to round. Apex: Rounded, cuspidate. Base: Attenuate. Margin: Entire. Texture, upper and lower surfaces: Smooth, glabrous. Color: When opening, upper surface: Close to 53A. When opening, lower surface: Close to 53B. Fully opened, upper surface: Close to 53A. Fully opened, lower surface: Close to 60B to 60C.

*Sepals.*—Quantity per flower: Typically five. Length: About 3.1 cm. Width: About 1.3 cm. Shape: Lanceolate. Apex: Pointed. Base: Truncate. Texture, upper and lower surfaces: Pubescent. Color: When opening, upper surface: Close to 146C. When opening, lower surface: Close to 183A; towards the margins and base, close to 144A. Fully opened, upper surface: Close to 143C. Fully opened, lower surface: Close to 164A; towards the margins and base, close to 144A.

*Peduncles.*—Strength: Strong; flexible. Aspect: Mostly erect. Length: About 3.3 cm. Diameter: About 5.7 mm. Texture: Smooth. Color: Close to 146A tinted with N199A.

*Pedicels.*—Strength: Strong; flexible. Aspect: About 40° from vertical. Length: About 4.1 cm. Diameter: About 3.1 mm. Texture: Smooth. Color: Close N199A.

*Reproductive organs.*—Stamens: Quantity: About 160 per flower. Anther length: About 2.2 mm. Anther shape: Reniform. Anther color: close to 161B and N34C. Pollen amount: Abundant. Pollen color:

162A. Pistils: Quantity: About 111 per flower. Pistil length: About 1.3 cm. Stigma shape: Broadly reniform. Stigma color: Close to 160A. Style length: About 8.4 mm. Style color: Close to 145C. Ovary color: Close to 155A. Receptacle shape: Cup-shaped. Seeds: Length: About 7.6 mm. Diameter: About 4.3 mm. Color: Close to 16D to 2D. Fruits: Length: About 2.6 cm. Diameter: About 2 cm. Color: N163B.

Pathogen/pest resistance: Plants of the new Rose have been observed to be resistant to *Botrytis*. Plants of the new Rose have not been observed to be resist to pests and other pathogens common to Roses.

Temperature tolerance: Plants of the new Rose have been observed to tolerate temperatures ranging from 0° C. to 35° C.

It is claimed:

1. A new and distinct Rose plant named 'Esm Fant' as illustrated and described.

* * * * *

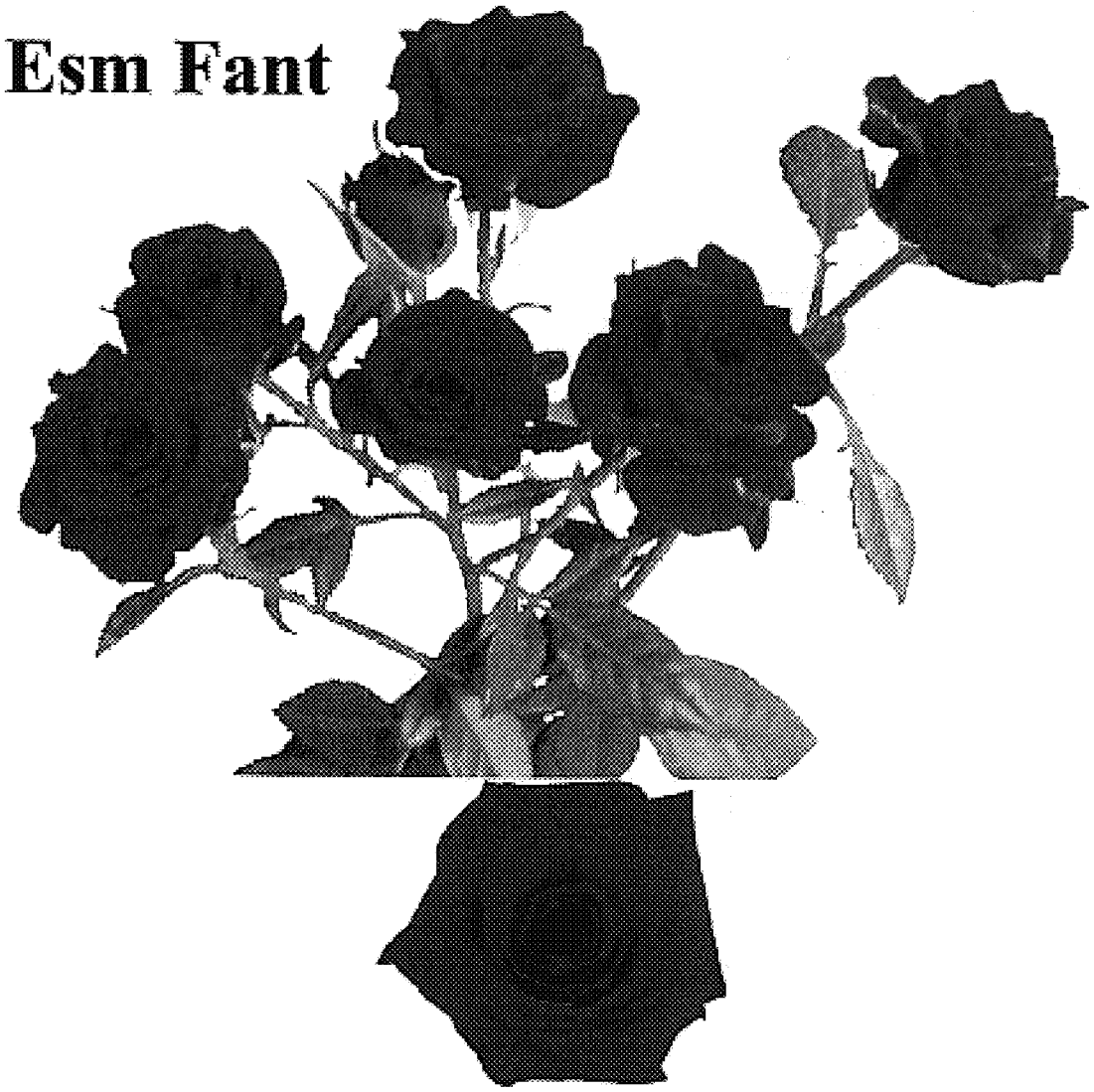
Esm Fant